United States Patent
Reiner et al.

(10) Patent No.: US 6,630,352 B1
(45) Date of Patent: Oct. 7, 2003

(54) STERILANT CHALLENGE DEVICE FOR A STERILIZATION MONITORING SYSTEM

(75) Inventors: Hackler Reiner, Krefeld (DE); Robbert-Jan Hermsen, Doetinchem (NL); Wolfgang Kaps, Kaarst (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/582,364

(22) PCT Filed: Dec. 22, 1998

(86) PCT No.: PCT/US98/27504

§ 371 (c)(1),
(2), (4) Date: Mar. 28, 2001

(87) PCT Pub. No.: WO99/32160

PCT Pub. Date: Jul. 1, 1999

(30) Foreign Application Priority Data

Dec. 22, 1997 (GB) .............................................. 9727533
Sep. 18, 1998 (GB) .............................................. 9820029

(51) Int. Cl.[7] .............................. A61L 2/00; A61L 2/26
(52) U.S. Cl. ................................. 436/1; 436/2; 422/61; 422/26; 422/295; 116/216
(58) Field of Search ............................ 422/56, 58, 61, 422/26, 295; 436/1–3; 116/216

(56) References Cited

U.S. PATENT DOCUMENTS

| | | |
|---|---|---|
| 4,115,068 A | 9/1978 | Joslyn |
| 4,594,223 A | 6/1986 | Dyke et al. |
| 5,066,464 A | 11/1991 | Augurt |
| 5,270,217 A | 12/1993 | Dyke |
| 5,565,634 A | 10/1996 | Graessle et al. |

FOREIGN PATENT DOCUMENTS

| | | |
|---|---|---|
| EP | 0 419 282 B1 | 7/1993 |
| EP | 0 421 760 B1 | 3/1994 |
| GB | 9727533.3 | 12/1997 |
| WO | WO 93/21964 | 11/1993 |
| WO | WO 97/12637 | 4/1997 |

Primary Examiner—Lyle A. Alexander
(74) Attorney, Agent, or Firm—Daniel R. Pastirik

(57) ABSTRACT

A sterilant challenge device (1), for use in testing the efficiency of the air removal stage of a sterilization cycle in a sterilizer, includes a tube (2) of thermally-insulating material, the bore of which is closed at one end (3) and open at the other for the entry of sterilant. A plurality of thermally-conductive masses (4) is located around the tube (2) and thermally-separated from one another by air gaps (14), and a temperature sensor is located in an opening (16) in one of the masses adjacent the closed end of the tube. An outer casing (5) defines an air space around the thermally-conductive masses and thermally insulates the masses from the heat in the sterilizer.

15 Claims, 6 Drawing Sheets

STERILANT CHALLENGE DEVICE FOR A STERILIZATION MONITORING SYSTEM

The present invention relates to monitoring systems for determining the efficacy of sterilization cycles in sterilizers and, more especially, to a sterilant challenge device for use in such a system.

One of the factors that has a detrimental effect on the efficacy of a sterilization cycle is the presence, in the sterilization chamber, of air or non-condensable gases which can collect in pockets in the load that is being sterilized and prevent the load from being adequately exposed to sterilant. In a steam sterilizer, for example, the object of the sterilization process is to bring steam of a suitable quality and at an appropriate temperature into contact with all surfaces of the load. Any air/gas pockets that collect within the load create a barrier to steam penetration, particularly when the load is made up of porous materials such as hospital linens or fabrics, and prevent effective sterilization from taking place.

Sterilization monitoring systems and methods which make use of a simulated porous load are known. The simulated load is located in the sterilization chamber and the extent to which sterilant penetrates the load during a sterilization cycle is monitored and used to determine whether or not the cycle was effective.

One form of challenge device is described in EP A 0 419 282. That device includes a container having top and bottom walls with a porous packing material disposed within the container. The packing material challenges the penetration of the sterilant by providing a restricted pathway which acts to impede the flow of the sterilant through the device. A removable lid seals the bottom end of the container, while a hole in the top wall of the container allows for the downward ingress of steam into the packing material within the container. The device includes a chemical indicator for detecting sterilant penetration. If sterilant successfully penetrates the packing material, the chemical indicator sheet will undergo a complete colour change. If the sterilant does not sufficiently penetrate the packing material, the chemical indicator will not undergo a complete uniform colour change, thereby indicating inadequate air removal or the presence of non-condensable gas.

Other challenge devices for use in steam or gas sterilizers are described in EP-A-0 421 760; U.S. Pat. No. 5,066,464; WO 93/21964 and U.S. Pat. No. 5,270,217. In each of those devices, sterilant from the sterilization chamber must cross some form of physical barrier before it reaches a sterilant sensor within the test pack. WO 93/21964, for example, describes a test unit comprising a test cavity having an opening at one end to permit entrance of ambient gases, a temperature sensor at the other end and a heat sink (for example gauze, felt, open-celled polymer foam) between the temperature sensor and the opening.

U.S. Pat. No. 4,594,223 describes various devices for indicating the presence of non-condensable gas in a sterilization chamber. In one version, a heat and humidity sensor is located at the lower end of an elongate cavity which is open at the upper end. Heat sink material in the form of fibrous insulating material is located within the cavity between the opening and the sensor. In another version, the path between the opening and the sensor is through a heat sink block in the form of a mass of aluminium surrounded by insulation, rather than through fibrous heat sink material.

U.S. Pat. No. 4,115,068 describes an air indicating device for use in sterilizers, comprising an upright tube which is open at its bottom end and closed at its top end. The tube is made of heat insulating material lined on its interior surface with a heat conducting material. A thermal indicator strip extends axially into the tube.

Another known arrangement for challenging the penetration of sterilant to a particular location comprises a very long (typically, 1.5 m) stainless steel tube with a narrow bore (typically, 2.0 mm) which provides the only access for sterilant to the predetermined location.

WO 97/12637 describes a challenge device which comprises a tube of thermally-insulating material, the bore of which is closed at one end but open at the other for the entry of sterilant, and a plurality of thermally-conductive masses located around the tube and thermally-separated from one another lengthwise of the tube by air gaps. When the device is in use in a sterilization chamber, the penetration of sterilant along the bore of the tube is inhibited by the accumulation of air and/or non-condensable gases within the bore resulting from condensation on the walls of the latter. By measuring the temperature in one of the thermally-conductive masses located towards the closed end of the tube, the presence or absence of sterilant in the adjacent region of the bore of the tube can be detected enabling the efficacy of a sterilization cycle to be determined.

The present invention is concerned with the provision of an improved challenge device for a sterilization monitoring system, which is of comparatively simple construction but which will function reliably to enable ineffective sterilization cycles to be detected.

The present invention provides a sterilant challenge device for use in a sterilizer for determining the efficacy of the air removal stage of a sterilization cycle, the device comprising a tube of thermally-insulating material, the bore of the tube defining a free space which is open at one end for the entry of sterilant and is closed at the other end; and a heat sink portion which surrounds the tube and, when the device is in use in a sterilizer, receives heat preferentially from the bore of the tube whereby the penetration of sterilant along the bore of the tube during a sterilization cycle is inhibited through the accumulation of air and/or non-condensable gas within the free space resulting from condensation on the wall of the bore; the device also comprising means for mounting a sensor to detect the presence of sterilant at, or adjacent, the closed end of the tube; wherein the wall of the bore is provided with a surface structure which, during a sterilization cycle, directs condensate that forms on the wall towards the open end of the bore.

Preferably, the heat sink portion comprises a plurality of thermally-conductive masses located around the tube along the length of the latter; the masses being thermally-separated from one another lengthwise of the tube and being surrounded by thermal insulation.

BRIEF DESCRIPTION OF THE DRAWINGS

By way of example only, embodiments of the invention will be described with reference to the accompanying drawings, in which:

FIG. 1 shows a sterilant challenge device 1 suitable for use in a system for testing the efficacy of a sterilization cycle in a steam sterilizer or in a low temperature gas sterilizer in which sterilization is carried out using a microbiocidal agent in the presence of moisture. The device 1 is intended to be located in the sterilization chamber of the sterilizer to provide a challenge path along which sterilant (for example, steam) from within the chamber must pass before it can be detected by a sensor at a predetermined location within the device. If the presence of sterilant at the predetermined location is not detected by the sensor during a sterilization cycle (indicating that the conditions within the sterilization chamber have not enabled sterilant to penetrate the challenge path), the sterilization cycle is judged to be ineffective.

Figure 1:
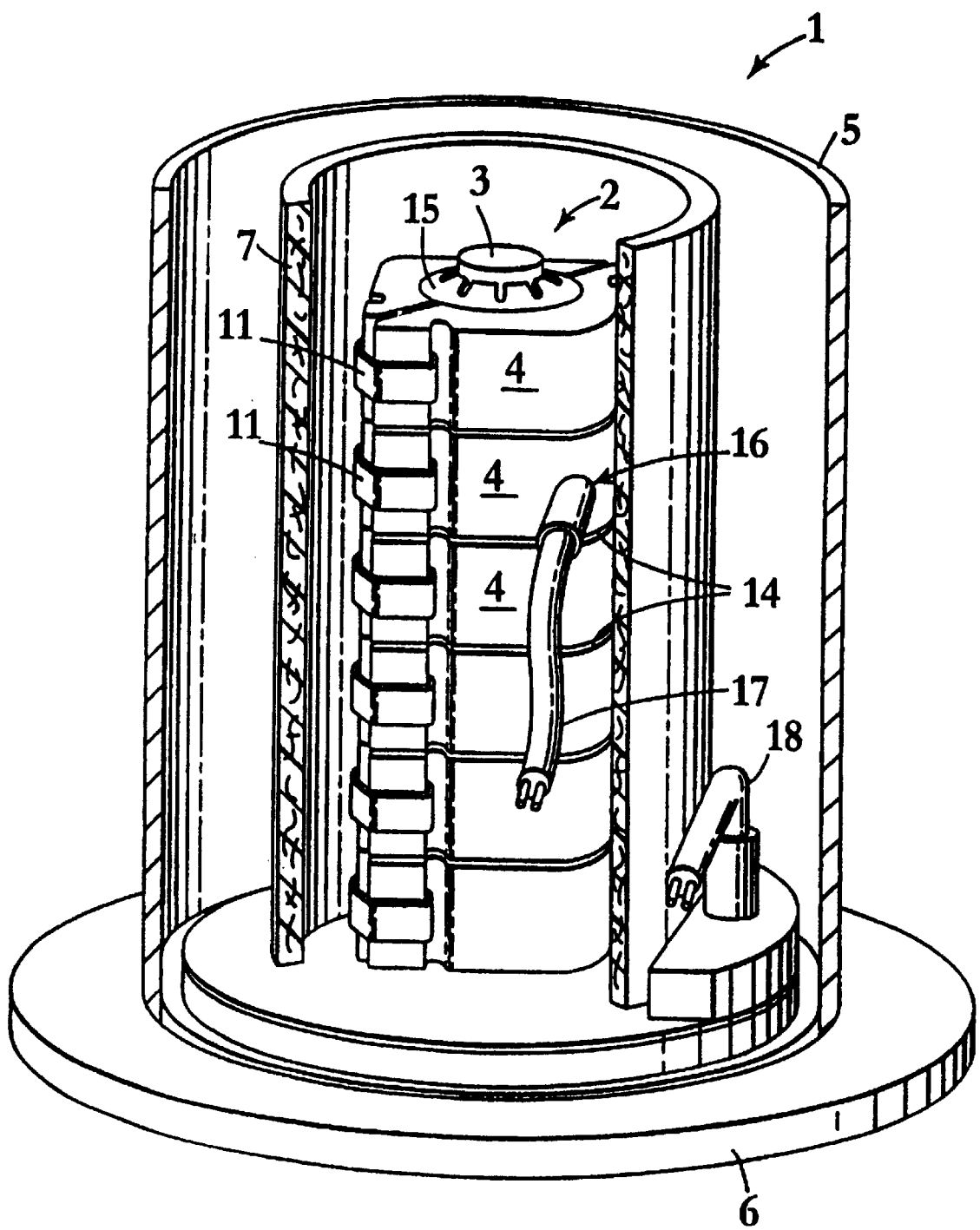
FIG. 1 is a perspective view, partly cut away, of a sterilant challenge device in accordance with the invention.

The challenge device 1 includes a central tube 2, with a bore (not visible in FIG. 1) of generally constant cross-section, which is closed at the upper end 3 and open at the lower end (not visible). The tube 2 is formed of a thermally-insulating material and is surrounded by a plurality of thermally-conductive blocks 4 located side-by-side along the length of the tube. The challenge device is provided with an outer casing 5 which is shown as being open at the upper end but which, in use, would be provided with an end plate to provide a hermetic seal. Access to the bore within the tube 2 is provided through a lower end plate 6 which surrounds the open end of the tube and supports both the thermally-conductive blocks 4 and the outer casing 5. An optional thermally-insulating cylinder 7 of open-cell foam material may be located around the thermally-conductive blocks 4, inside the outer casing 5.

Figure 2:
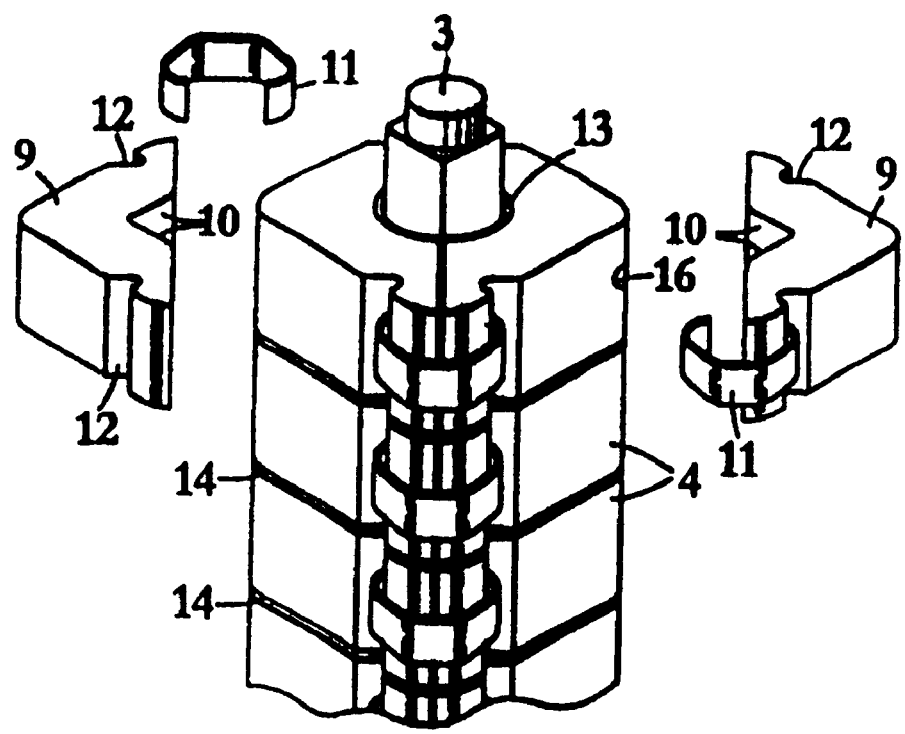
FIG. 2 is a perspective view, partly exploded, of a part of the device of FIG. 1.

The bore 8 of the tube 2 (visible in FIG. 3) has a generally circular cross-section, except that the wall of the bore is formed with longitudinally-extending grooves as will be described in greater detail below. The outer cross-section of the tube 2, except immediately adjacent the closed end 3, is square. The thermally-conductive blocks 4, which form a heat sink, are positioned on the square-sectioned part of the tube 2, each block being formed in two halves 9 (see FIG. 2) having flat inner surfaces 10 corresponding to two of the outer sides of the tube. When in position on the tube 2, the two halves 9 of each block 4 are held together by two spring clips 11 which engage in recesses 12 in the outer surfaces of the block. The square outer shape of the tube 2 and the corresponding shape of the inside of the blocks 4 provide good thermal contact between the tube and the blocks, and the spring clips 11 ensure that the good thermal contact is maintained while accommodating the different rates of expansion/contraction of the tube and the blocks when the challenge device 1 is in use in a sterilization chamber.

Although the blocks 4 are located side-by-side along the length of the tube 2, they do not contact one another but are spaced apart slightly by thermally-insulating O-rings 13 (one of which is visible in FIGS. 2 and 3) located between adjacent blocks. The resulting air spaces 14 between the blocks cause the blocks to be thermally-separated from each other and prevent heat being transmitted through the blocks along the length of the tube 2. When all the blocks 4 are in position on the tube 2, they are secured in place by a circular clip 15 (FIG. 1) fitted over the end of the tube adjacent the end block.

The penultimate block 4 on the tube 2 is formed with a circular opening 16 in which a temperature sensor, preferably (but not essentially) a platinum resistance thermometer, is located when the challenge device 1 is in use. The electrical lead 17 of the temperature sensor can be seen in FIG. 1.

As described below, the challenge device 1 can be used in a test pack of the type comprising (in addition to the challenge device) a second temperature sensor arranged to measure the temperature outside the test pack (i.e. in the sterilization chamber in which the test pack is located when in use), and electronic circuitry which, on the basis of the measurements from the temperature sensors, functions to determine whether or not a sterilization cycle is satisfactory. With a view to being used in such a test pack, the challenge device 1 is already provided with a second temperature sensor for measuring the temperature outside of the test pack and the electrical lead 18 of that second temperature sensor can also be seen in FIG. 1, extending into the space between the outer casing 5 and the thermally-conductive blocks 4.

During a sterilization cycle, sterilant can enter the bore 8 of the challenge device 1 only through the lower (open) end of the tube 2. Because the tube 2 is thermally insulated from the heat in the sterilization chamber by the airspace within the casing 5 (and by the thermally-insulating cylinder 7 when present), and because the tube is formed from a thermally-insulating material, the bore 8 will receive heat primarily from sterilant entering the bore. As a result, the temperature of the wall of the bore 8 will remain below that of the sterilization chamber and sterilant which enters the bore will condense on the wall and not penetrate immediately to the end of the bore, resulting in an accumulation of air or non-condensable gas within the bore. That pocket of air or non-condensable gas will inhibit the penetration of sterilant to the end of the bore 8 and will influence the temperature at the closed end of the tube 2 and in the surrounding thermally-conductive blocks 4. In this respect, it will be noted that the blocks 4 are prevented from transmitting heat to one another by the presence of the air gaps 14. Accordingly, by measuring the temperature of the blocks 4 at the closed end of the tube 2 in relation to the temperature within the sterilization chamber, it can be determined if sterilant has penetrated to the end of the tube (indicating that the sterilization cycle has been effective) or if a pocket of air or non-condensable gas remains at the end of the tube (indicating that the sterilization cycle has not been effective).

The thermally-insulating material from which the tube 2 is formed should be steam tight, and stable under the conditions encountered in a sterilization chamber. Preferably, the thermally-insulating material is a Liquid Crystal Polymer (LCP), most preferably a complete aromatic copolyester with a 25% by weight graphite content. The thermally-conductive material from which the blocks 4 are formed is preferably aluminium. The O-rings 13 between the blocks may be formed from rubber and the outer casing 5 of the device may be formed from stainless steel. The tube 2 is typically about 115 mm long, with an internal (i.e. bore) diameter of about 6 mm and an external dimension of about 10 mm square. The blocks 4 are typically about 28 mm square, and about 15 mm wide. Six such blocks are shown in FIG. 1 and, typically, are positioned with a spacing 14 of about 1 mm between adjacent blocks. Alternatively, a larger number of thinner blocks could be used (for example, twelve blocks with a width of 7 mm).

A challenge device of the type shown in FIG. 1 and described above is disclosed in WO 97/12637, to which reference may be made for further information if required.

Figure 3:
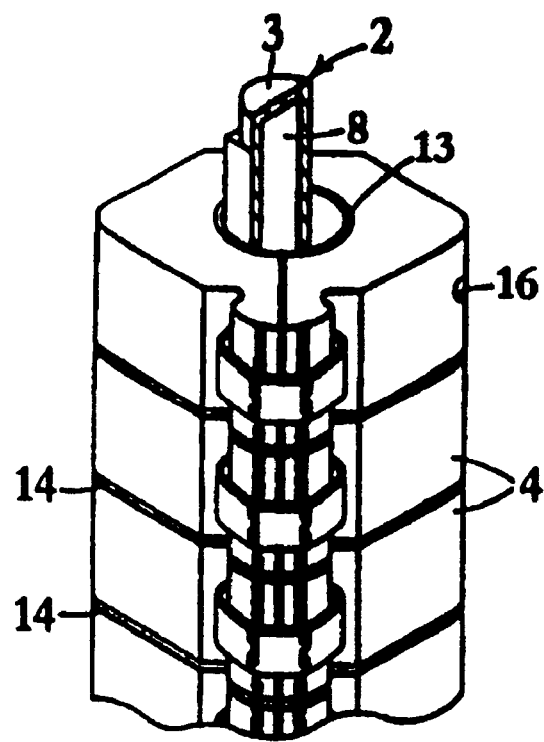
FIG. 3 is a view similar to FIG. 2 but partly in longitudinal cross-section and with the exploded components omitted.

It was mentioned above that the wall of the bore 8 in the tube 2 is formed with longitudinally-extending grooves (not shown in FIG. 3). Those grooves, which will now be described in greater detail, are provided to ensure that condensate which forms on the wall of the bore 8 during sterilization cycles drains out of the bore freely and does not form droplets which could accumulate and block the bore, potentially giving rise to aberrations in the measurements made by the temperature sensor located in the opening 16.

Figure 4:
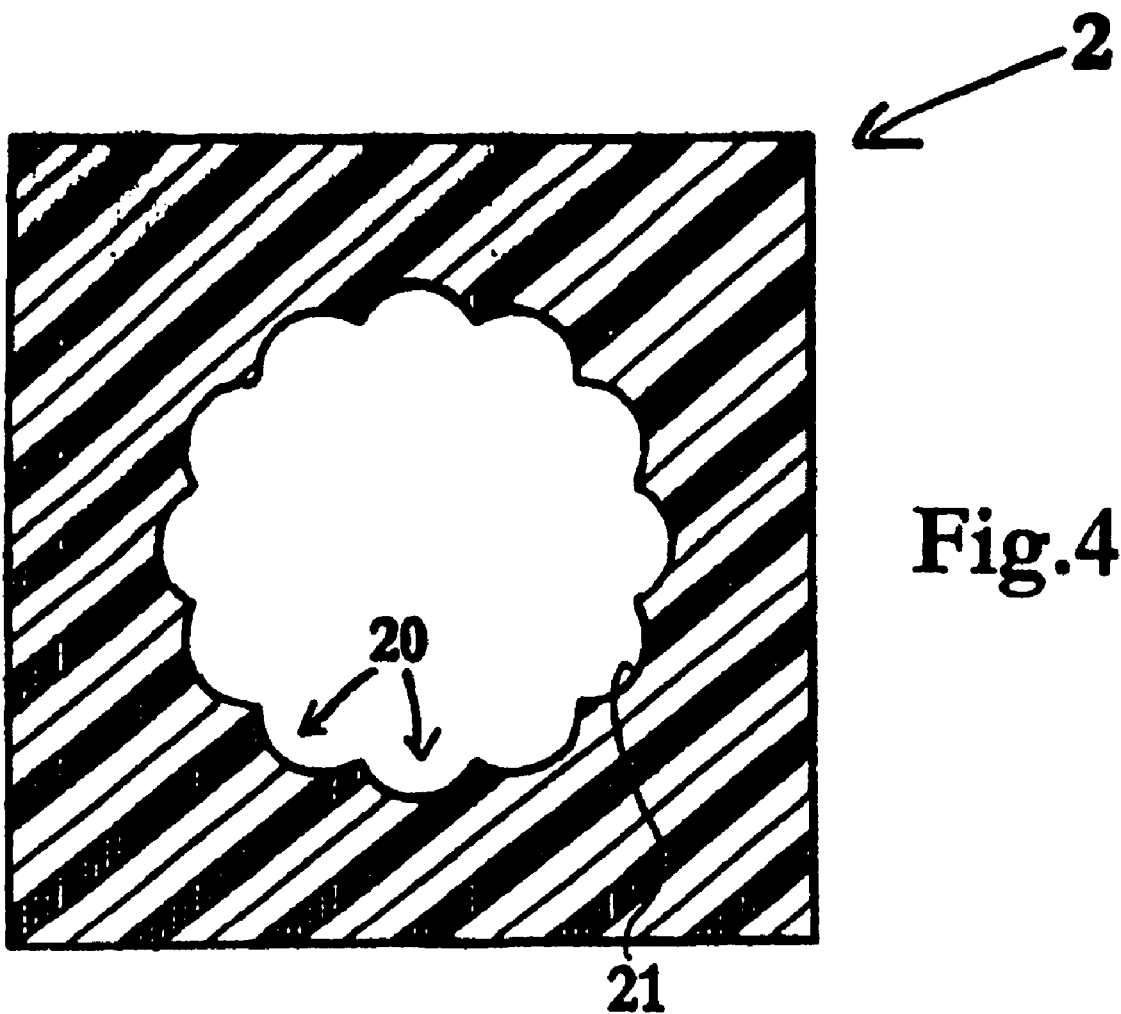
FIG. 4 is a transverse cross-section through a component of FIGS. 2 and 3.

One suitable groove structure is illustrated in FIG. 4 which is a transverse cross-section through the tube 2. The grooves 20 extend longitudinally of the tube and are positioned one adjacent another around the whole surface of the wall 21 of the bore 8. Each groove 20 has a substantially semi-circular transverse cross-section and a width, across the top of the groove (i.e. the diameter of the semi-circle), which is preferably in the range of from 1.0 to 1.5 mm but could be as large as 3.0 mm. Any moisture that condenses on the wall 21 during a sterilization cycle will lie in one of the grooves 20 and will tend to move along the groove, rather than remain stationary and increase in size. In particular, the vertical orientation of the tube 2 means that the condensate will tend to move downwardly along the grooves 20 towards the open end of the tube.

Figure 5:
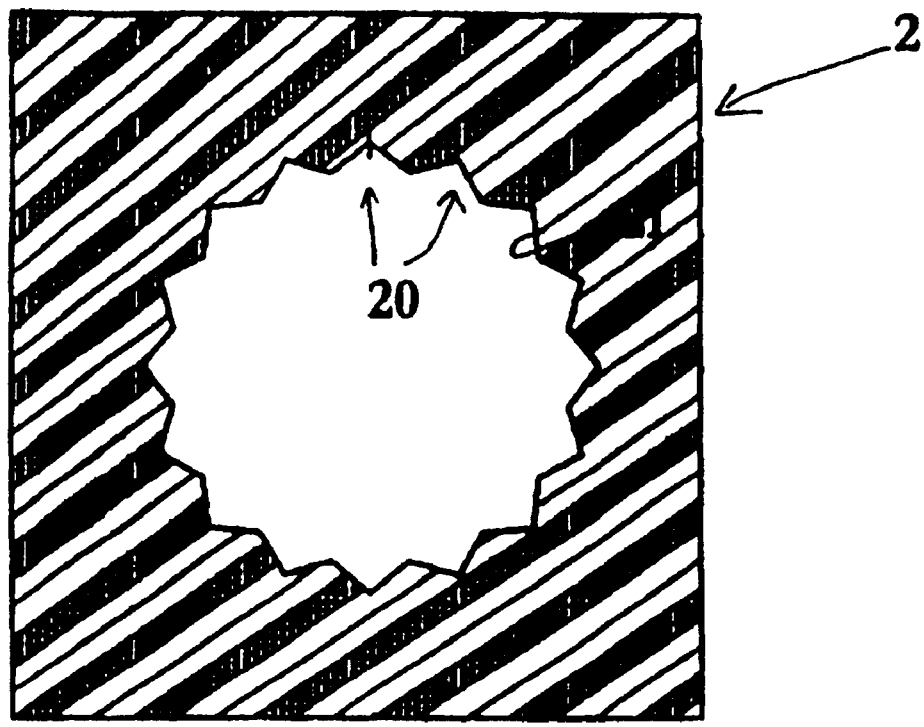
FIGS. 5 and 6 are similar to FIG. 4 but show alternative cross-sections.
Figure 6:
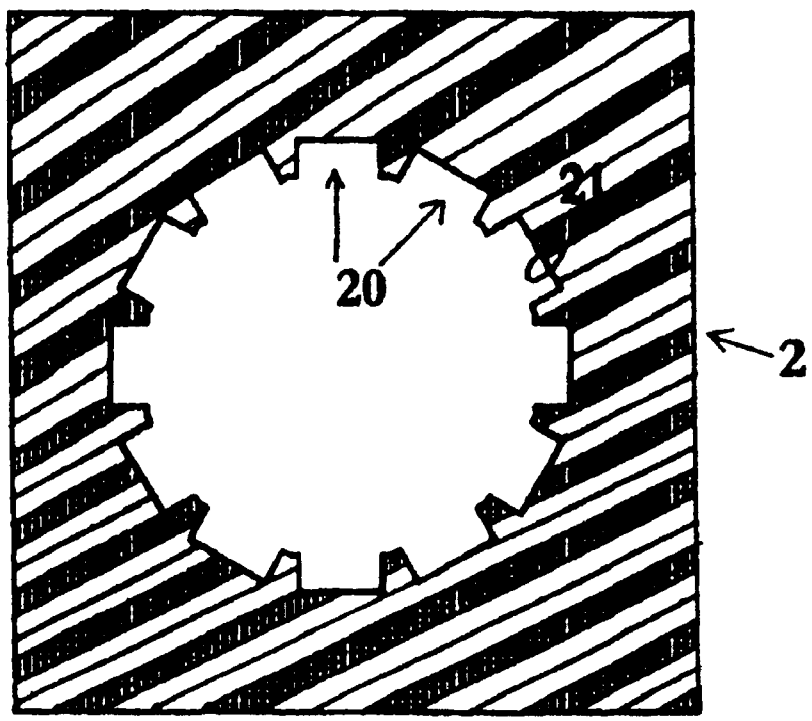

Alternative groove structures are illustrated in FIGS. 5 and 6. In each case, as in FIG. 4, the grooves 20 extend longitudinally of the tube and are positioned one adjacent another over the whole surface of the wall 21 of the bore 8. In FIG. 5, the grooves 20 are shown as having a substantially triangular cross-section, and in FIG. 6 they are shown as having a substantially rectangular cross-section, and in each case the width across the top of a groove (i.e. the third side of the triangle in FIG. 5 or the fourth side of the rectangle in FIG. 6) is preferably in the range 1.0 to 1.5 mm but could be as large as 3.0 mm.

It will be appreciated, however, that grooves could be used having cross-sectional shapes and dimensions which differ from those shown for the grooves 20 in FIGS. 4 to 6, and that it is not essential that all of the grooves have the same cross-sectional shape. In each case, however, the shape and size of the grooves must be selected to ensure that adhesion and/or capillary forces acting on moisture which condenses on the wall 21 of the bore 8 are not high enough to prevent the moisture moving downwardly along the grooves 20, under the effect of gravity, towards the open end of the tube 2.

As a further alternative, the groove structure in the wall 21 of the bore 8 can be replaced by any structure, including a simple roughening of the wall, which will have the effect of preventing the formation of droplets of condensate which might accumulate and block the bore. However, grooved structures of the type illustrated in FIGS. 4 to 6 offer the advantage of directing the condensate to the mouth of the tube 2, where it can drain out of the bore 8.

The tube 2 is advantageously a moulded component.

Figure 7:
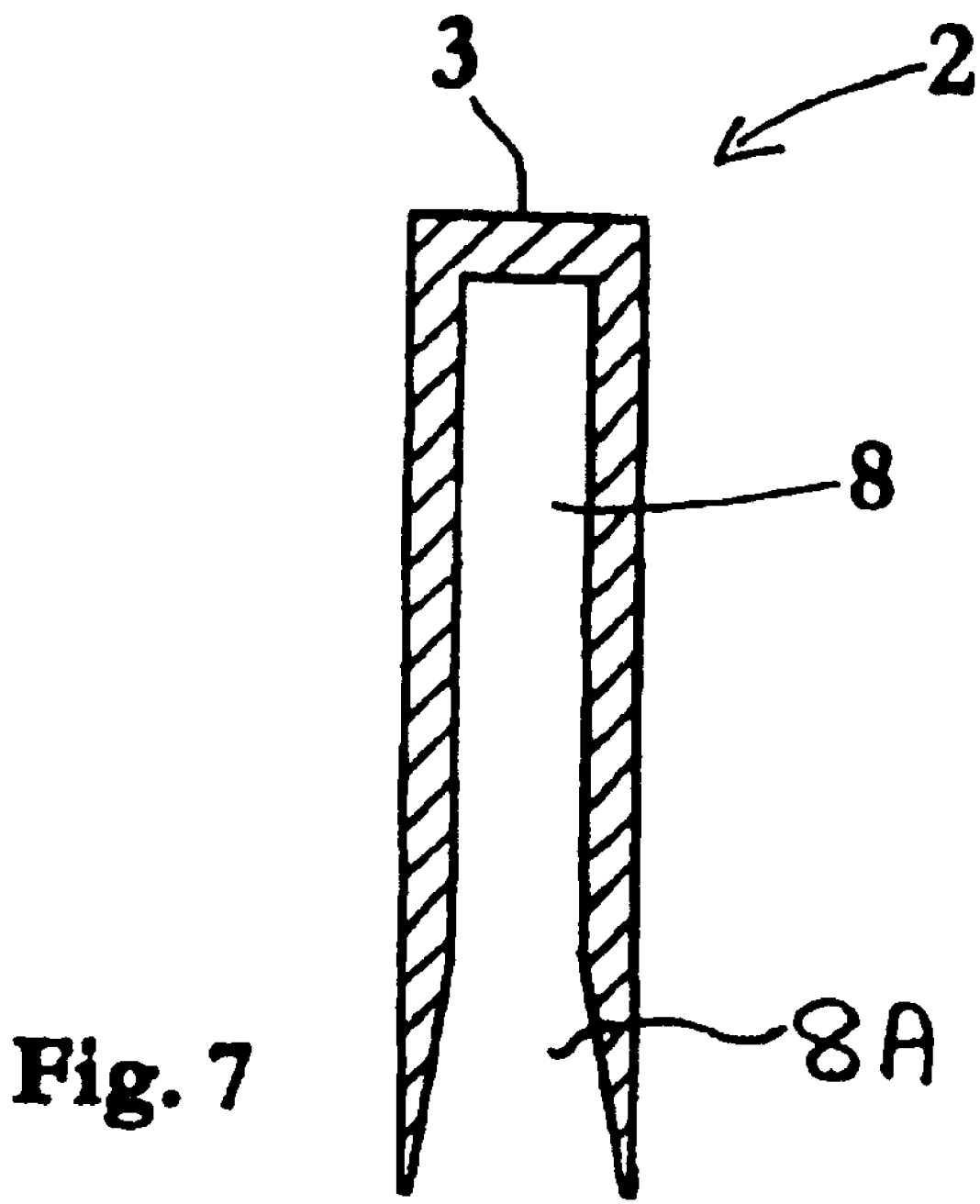
FIG. 7 is a longitudinal cross-section through the component of FIG. 4.

To ensure that condensate can drain freely from the mouth of the tube 2, the latter is preferably shaped so that the bore 8 flares outwards, adjacent the open end thereof, in the direction towards the open end as shown in FIG. 7. The grooves 20 may be omitted from this flared portion 8A. The angle at which the bore flares outwards is selected having regard to the dimensions of the tube 2 to ensure that, at its lower end, the bore is too large to become blocked by droplets of condensate that may remain on the lower end of the tube and be drawn back into the tube by adhesion and/or capillary forces. That might occur, for example, if the flow of condensate from within the tube is temporarily interrupted during a specific phase of a sterilization cycle. Typically, for that purpose the diameter of the bore 8 at the lower end of the tube 2 should be at least 8mm and, preferably, at least 10 mm. In addition, the length of the flared portion 8A is advantageously sufficient to prevent any back-flow of condensate to the inner (i.e. straight) section of the bore 8. In the case in which the tube 2 is about 115 mm long, with an internal diameter of about 6 mm, it has been found that the best results are obtained when the bore 8 flares outwards at an angle in the range of from 10° to 20° over a length of about 10 mm.

Figure 8:
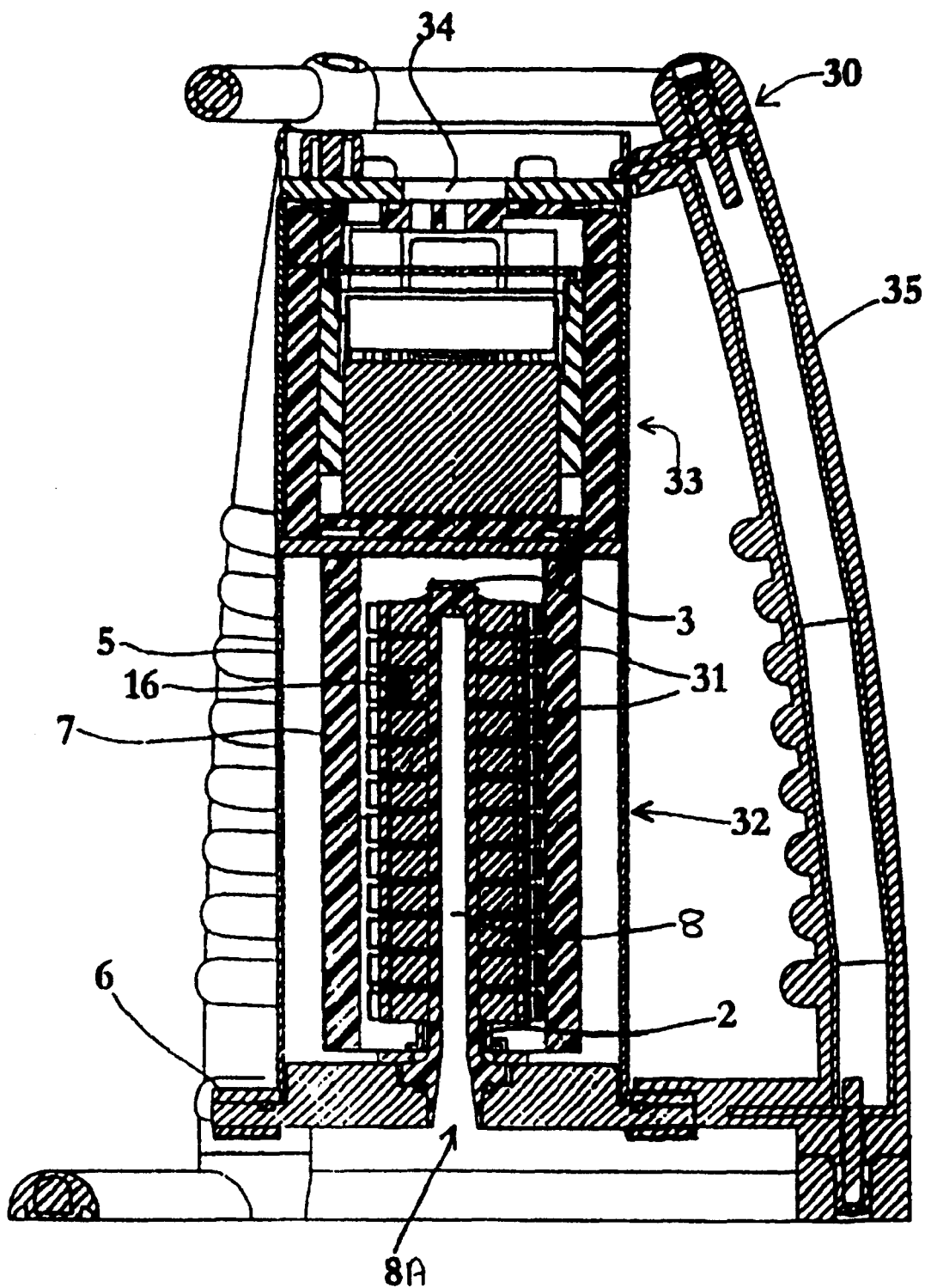
FIG. 8 is a longitudinal cross-section through an electronic sterilization monitoring device incorporating a challenge device of the type shown in FIG. 1.

A sterilization monitoring device 30 incorporating a challenge device of the type described above is shown in FIG. 8. The challenge device is indicated in FIG. 8 by the reference 32 and is located in the lower part of the monitoring device 30. It is of the same general construction as the challenge device shown in FIG. 1 except that the thermally conductive blocks 4 are replaced by a large number of thinner blocks 31. Similar components of the challenge devices 1 and 30 carry the same reference numerals in FIGS. 1 to 3 and 8.

The leads (17, 18 in FIG. 1) of the two temperature sensors of the challenge device 30 are connected to an electronic memory in the upper part 33 of the monitoring device. The memory records the information from the temperature sensors and provides information to a microprocessor (also in the upper part 33 of the monitoring device) for determining if a particular sterilization cycle has been effective. A visual signal giving the results of that determination (i.e. a pass/fail decision) is provided at the end of the sterilization cycle by a pair of LEDs located at the upper end of the upper part 33 of the monitoring device. Those LEDs, together with a second pair which indicates the operational status of the monitoring device, are visible through a window 34 in the upper end face of the device. In addition, when the monitoring device 30 has been removed from the sterilization chamber, recorded information about a sterilization cycle may be transferred from the test pack to outside hardware for further analysis and/or documentation. The information is transferred in the form of pulses of infrared radiation generated by an infrared LED within the device 30 and also transmitted through the window 34. Also provided in this upper part 33 of the monitoring device is an infrared receiver enabling certain functions of the monitoring device to be initiated by infrared signals transmitted through the window 34 from outside.

The monitoring device 30 is provided with a protective framework 35 which not only protects the device against impacts but also facilitates the handling of the device during use.

A monitoring device of the type shown in FIG. 8 is disclosed in our co-pending UK Patent Application No. 9727533.3, filed Dec. 22, 1997, to which reference may be made for further information, if required. It will be appreciated, from the above description of the challenge device 32 (and, in particular of the tube 2) that condensate which forms on the wall of the bore 8 will be directed by the grooves in the wall towards the lower end of the challenge device and will drain freely from the shaped open end of the tube. As a result, any risk of the tube being blocked by condensate is avoided and the monitoring device can function consistently and reliably throughout a large number of sterilization cycles.

What is claimed is:

1. A steriliant challenge device for use in a sterilizer for determining the efficacy of the air removal stage of a sterilization cycle, the device comprising a tube of thermally-insulating material, the bore of the tube having a wall extending therethrough and defining a free space which is open at one end for the entry of sterilant and is closed at the other end; and a heat sink portion which surrounds the tube and, when the device is in use in a sterilizer, receives heat preferentially from the bore of the tube whereby the penetration of sterilant along the bore of the tube during a sterilization cycle is inhibited through the accumulation of air and/or non-condensable gas within the free space resulting from condensation on the wall of the bore; the device also comprising means for mounting a sensor to detect the presence of sterilant at, or adjacent, the closed end of the tube; wherein the wall of the bore is provided with grooves which, during a sterilization cycle, directs condensate that forms on the wall towards the open end of the bore.

2. A device as claimed in claim 1, in which the grooves extend parallel to the longest axis of the tube and, during a sterilization cycle, direct condensate that forms on the wall toward the open end of the bore.

3. A device as claimed in claim 2, in which the grooves are positioned one adjacent another over the whole surface of the wall of the bore.

4. A device as claimed in claim 2, in which each groove has a semicircular, triangular or rectangular transverse cross-section.

5. A device as claimed in claim 2, in which the width of each groove across the top thereof is in the range of from 1.0 to 3.0 mm, preferably 1.0 to 1.5 mm.

6. A device as claimed in claim 1, in which the open end of the bore is widened to prevent the bore being blocked by droplets of condensate drawn back into the tube from the open end.

7. A device as claimed in claim 6, in which the bore flares outwards, adjacent the open end thereof, in the direction towards the open end.

8. A device as claimed in claim 7, in which the bore flares outwards to a diameter of at least 8.0 mm.

9. A device as claimed in claim 7, in which the bore flares outwards to a diameter of at least 8.0 mm.

10. A device as claimed in claim 1, in which the tube is a moulded plastic component.

11. A device as claimed in claim 1 in which the heat sink portion comprises a plurality of thermally-conductive masses located around the tube along the length of the latter; the masses being thermally-separated from one another lengthwise of the tube and being surrounded by thermal insulation.

12. A device as claimed in claim 11, in which the thermal insulation surrounding the tube and thermally-conductive masses is provided by an outer casing which surrounds the tube and thermally-conductive masses and is separated therefrom by an air space.

13. A device as claimed in claim 11, including a temperature sensor located in one of the thermally-conductive masses at, or adjacent, the closed end of the tube, to detect the temperature in the thermally-conductive mass and thereby detect the presence of sterilant in the adjacent region of the bore of the tube.

14. A device as claimed in claim 13, in combination with a second temperature sensor positioned to detect the temperature in a sterilization chamber in which the device is located.

15. A sterilization monitoring device including a sterilant challenge device as claimed in claim 13, and electronic means electrically connected to the temperature sensor(s) and operable to determine whether or not sterilant has penetrated adequately to the said adjacent region of the bore of the tube.

* * * * *

UNITED STATES PATENT AND TRADEMARK OFFICE
CERTIFICATE OF CORRECTION

PATENT NO. : 6,630,352 B1
DATED : October 7, 2003
INVENTOR(S) : Hackler, Reiner

It is certified that error appears in the above-identified patent and that said Letters Patent is hereby corrected as shown below:

Title page,
Item [12], replace "Reiner et al." with -- Hackler et al. --;
Item [75], Inventors, replace "Hackler Reiner" with -- Reiner Hackler --
Item [56], References Cited, U.S. PATENT DOCUMENTS, replace "5,565,634" with -- 5,564,634 --;

Signed and Sealed this

Twenty-seventh Day of July, 2004

JON W. DUDAS
*Acting Director of the United States Patent and Trademark Office*